United States Patent [19]

Sawada et al.

[11] Patent Number: 4,604,353
[45] Date of Patent: Aug. 5, 1986

[54] METHOD FOR PRODUCING CONJUGATED URSODEOXYCHOLIC ACIDS BY MEANS OF MICROBIAL TRANSFORMATION

[75] Inventors: Haruji Sawada; Masaaki Watanuki, both of Tokyo, Japan

[73] Assignee: Kabushiki Kaisha Yakult Honsha, Tokyo, Japan

[21] Appl. No.: 583,426

[22] Filed: Feb. 24, 1984

[30] Foreign Application Priority Data

Mar. 4, 1983 [JP] Japan ................................ 58-035554

[51] Int. Cl.$^4$ ...................... C12P 33/06; C12R 1/645
[52] U.S. Cl. ...................................... 435/58; 435/911
[58] Field of Search ........................................... 435/58

[56] References Cited

U.S. PATENT DOCUMENTS

| | | | |
|---|---|---|---|
| 2,962,423 | 11/1960 | Feldman et al. | 435/58 |
| 3,060,101 | 10/1962 | Feldman et al. | 435/58 |
| 3,401,180 | 9/1968 | Pan et al. | 435/58 |
| 4,301,246 | 11/1981 | Despreaux et al. | 435/58 |

Primary Examiner—Alvin E. Tanenholtz
Attorney, Agent, or Firm—Wenderoth, Lind & Ponack

[57] ABSTRACT

A one step method of producing conjugated ursodeoxycholic acids from conjugated lithocholic acids by means of microbial transformation which comprises subjecting the conjugated lithocholic acids to the action of microorganisms which belong to Mortierella and which are capable of producing conjugated ursodeoxycholic acids from conjugated lithocholic acids.

5 Claims, 3 Drawing Figures

Conjugated ursodeoxycholic acid
(R= amino acid)

Conjugated lithocholic acid
( R= amino acid )
(II)

Conjugated
ursodeoxycholic acid
(I)

METHOD FOR PRODUCING CONJUGATED URSODEOXYCHOLIC ACIDS BY MEANS OF MICROBIAL TRANSFORMATION

FIELD OF THE INVENTION

The present invention relates to a method for producing conjugated ursodeoxycholic acids by means of microbial transformation, and more specifically to a method for producing one or more ursodeoxycholic acids conjugated with one or more amino acids (hereinafter referred to as conjugated ursodeoxycholic acids), the final products, which comprises subjecting one or more lithocholic acids conjugated with one or more amino acids (hereinafter referred to as conjugated lithocholic acids), the starting materials, to the action of one or more specific microorganisms having capability of producing conjugated ursodeoxycholic acids.

BACKGROUND OF THE INVENTION

FIG. 1 shows the general formula (I) showing the molecular structure of conjugated ursodeoxycholic acids, the final products of a method in accordance with the present invention. Referring to the Figure, a conjugated ursodeoxycholic acid is a bile acid wherein hydroxyl groups are located at $3\alpha$ and $7\beta$ positions thereof and the carboxyl group located in a side chain thereof is conjugated with an amino acid (including artificially produced amino acids).

Out of the conjugated ursodeoxycholic acids, tauroursodeoxycholic acid, a ursodeoxycholic acid conjugated with taurine, is the major substance of the gallbladder of a bear. This compound is a potential raw material for producing a ursodeoxycholic acid which has recently been employed as a cholagogue or a cholesterol solubilizer. In other words, a ursodeoxycholic acid can be produced by deconjugation of tauroursodeoxycholic acid. Since the supply of good gall-bladders of bears is fairly limited, it has been difficult to satisfy the entire quantity of medical demands with the aforementioned natural supply. This is the reason why chemical synthesis processes have been employed for producing ursodeoxycholic acid.

However, each of the chemical synthesis processes available in the prior art comprises plural complicated steps. Since the number of steps each of which is fairly complex, is sometimes as large as 7, they are involved with drawbacks wherein the process time is long, the process is complicated, the efficiency is inferior due to the purification processes each of which is needed after each individual step, and the yield is unsatisfactory due to side reactions each of which inevitably occurs accompanying each individual step.

Aiming at removal of these drawbacks, various one step methods have been proposed for producing ursodeoxycholic acid by means of microbial transformation wherein a $\beta$-hydroxyl group is introduced to be bonded with a carbon atom which is located at 7-position of the steroid nucleus (ring) of lithocholic acid.

We were successful in the development of a one step method for producing free ursodeoxycholic acid from free lithocholic acid, which comprises subjecting lithocholic acid, the starting material, to the action of any of the specific microorganisms or moulds belonging to Fusarium.

However, the transformational reaction substrate for this one step method for producing ursodeoxycholic acid is free lithocholic acid which does not necessarily readily dissolve in a cultivation medium and/or a reaction medium. Accordingly, this hydrophobic nature of the tranformational reaction substrate readily causes a low degree of microbial transformation in the aforementioned method, thus causing a low of yield, a slow reaction rate and a low degree of productivity.

In view of the fact that free ursodeoxycholic acid is converted, in the human body, to conjugated ursodeoxycholic acids, when it is internally applied, we assumed that some conjugated ursodeoxycholic acids would have medicinal value which is equivalent or superior to that of free ursodeoxycholic acid. Based on this assumption, and also based on the fact that conjugated lithocholic acids readily dissolve in water, we considered that a method for producing one or more conjugated ursodeoxycholic acids by means of microbial transformation which comprises subjecting one or more of the conjugated lithocholic acids to the action of one or more of the microorganisms which have capability for producing conjugated ursodeoxycholic acids, would remove the aforementioned drawbacks.

OBJECTS AND SUMMARY OF THE INVENTION

An object of the present invention is to provide a one step method for producing conjugated ursodeoxycholic acids, the final products, from conjugated lithocholic acids, the starting materials, by means of a microbial transformation technique, which overcomes the aforementioned drawbacks such as a lower degree of yield, a lower reaction rate and a lower grade of productivity.

A method in accordance with the present invention for producing a conjugated ursodeoxycholic acid from a conjugated lithocholic acid comprises subjecting a conjugated lithocholic acid to the action of any of the microorganisms or moulds belonging to Mortierella, whereby a $\beta$-hydroxyl group is introduced to be bonded with a carbon atom which is located at 7-position of the steroid nucleus (ring) of the conjugated lithocholic acid. The microbial transformation is shown in FIG. 2. Referring to the Figure, (I) represents the general formula of conjugated ursodeoxycholic acids which are produced by means of microbial transformation from conjugated lithocholic acids of which the general formula is represented by (II).

More specifically, the method in accordance with the present invention for producing a conjugated ursodeoxycholic acid comprises a step of bringing a conjugated lithocholic acid into contact with any part or parts of any of the microorganisms or moulds which have capability of producing conjugated ursodeoxycholic acids from conjugated lithocholic acids and which belong to Mortierella, typically *Mortierella ramanniana* var. *ramanniana* strain Y2-1 (hereinafter referred to as strain Y2-1) in any manner (in any type of reaction liquid, such as a nutrient medium, a reaction medium et al.).

Preferred embodiments of the present method are:
(1) A method for producing a conjugated ursodeoxycholic acid from a conjugated lithocholic acid, wherein the step of bringing a conjugated lithocholic acid into contact with the microorganism occurs in a medium in which the microorganism is cultivated and which further comprises a step of recovering a conjugated ursodeoxycholic acid.
(2) A method for producing a conjugated ursodeoxycholic acid from a conjugated lithocholic acid, (i) which further comprises a first preparatory step in which the microorganism is cultivated in a basal medium which readily allows good growth for the microorganism, a second preparatory step in which the microorganism is harvested and a third preparatory step in which a reaction medium containing the harvested microorganism is prepared, (ii) in which the step of bringing a conjugated lithocholic acid into contact with the microorganism occurs in this reaction medium, and (iii) which further comprises a finishing step in which the conjugated ursodeoxycholic acid is recovered.

(3) A method for producing a conjugated ursodeoxycholic acid from a conjugated lithocholic acid, (i) which further comprises a first preparatory step in which the microorganism is cultivated in an agar medium, typically in a potato agar medium or a malt extract agar medium until spores are formed, a second preparatory step in which the formed spores are collected and a third preparatory step in which a reaction medium which is a suspension containing the collected spores and a conjugated lithocholic acid is prepared, (ii) in which the step of bringing a conjugated lithocholic acid into contact with the microorganism occurs in this reaction medium, and (iii) which further comprises a finishing step in which the conjugated ursodeoxycholic acid is recovered.

Embodiment (1) includes a method wherein the conjugated lithocholic acid is added to the medium at various phases of cultivation.

Embodiment (2) includes a modification wherein the harvested microorganism is once stabilized with polyacrylamide, calcium arginate or the like, before it is brought into contact with a conjugated lithocholic acid, in addition to an example wherein the harvested microorganism is brought into contact with a conjugated lithocholic acid without delay after harvesting.

It is preferable for Embodiments (2) and (3) that the reaction medium contains a small quantity of energy source, specifically some organic materials, typically glucose, some other hydrocarbons, casein hydrolysate, yeast extract or the like.

Embodiment (3) includes a modification wherein the collected spores are once stabilized before being brought into contact with a conjugated lithocholic acid.

Since a conjugated lithocholic acid readily dissolves in water, the present invention provides a one step method for producing a conjugated ursodeoxycholic acid from a conjugated lithocholic acid by means of microbial transformation, wherein the yield, the reaction rate and the productivity are high.

In addition, a conjugated lithocholic acid which is the starting material for the microbial transformation which is the subject matter of the method in accordance with the present invention, has a unique molecular structure wherein a side chain which is bonded with an amino acid, effectively covers the external surface of the molecule excepting the carbon atom which is located at 7-position of the steroid nucleus (ring), thereby readily allowing a $\beta$-hydroxyl group access to the aforementioned 7-position of the steroid nucleus (ring) but prohibiting a hydroxyl group from approaching the other positions of the steroid nucleus (ring), thus protecting the molecule from any possibility of incurring side reactions. Due to this molecular structure of a conjugated lithocholic acid, a method for producing a conjugated ursodeoxycholic acid in accordance with the present invention results in an excellent yield which is as large as 95%.

Another advantage which accompanies the method in accordance with the present invention is that a large quantity of an conjugated lithocholic acid can be readily available, because it can be produced by mixing free lithocholic acid with one or more specific amino acids at a low temperature in dioxane containing tributylamine and ethyl chlorocarbonate, thus enabling the productivity to be increased for the method in accordance with the present invention. Although some quantity of free lithocholic acid remains unconjugated with the amino acid during the foregoing reaction, the remaining quantity of free lithocholic acid causes absolutely no adverse effects for the microbial transformation.

BRIEF DESCRIPTION OF THE DRAWINGS

The present invention, together with its various features and advantages, can be readily understood from the following more detailed description presented in conjunction with the following drawings, in which.

DETAILED DESCRIPTION (A) IDENTIFICATION OF STRAIN Y2-1

In the middle phase of cultivation of strain Y2-1 carried out at 27° C. on a malt extract agar medium, sporangia which confine many spores therein, grow at the end of sporangiophores which are 300–700 $\mu$m long. The sporangiophores grow on the side of a mycelia in the form of single extension or in the form of branched extension.

A small columella is recognized at the top end of the sporangiophore inside the opened sporangium in the last phase of cultivation. The spores have an oval shape, and their longer diameter varies between 3 $\mu$m and 5.5 $\mu$m and their shorter diameter varies between 1.5 $\mu$m and 2.5 $\mu$m.

The chlamydospores have various shapes, including a sphere, and many oil drops are recognized inside them.

No zygospores are recognized. This microorganism has a tendency to require thiamine.

Five-day cultivation carried out on a malt extract agar medium allows strain Y2-1 to grow up to a colony whose diameter ranges from 2.4 to 2.7 cm. The colony having the thickness ranging from 2 to 3 mm is velvety and vinaceousbrown.

Figure 1:
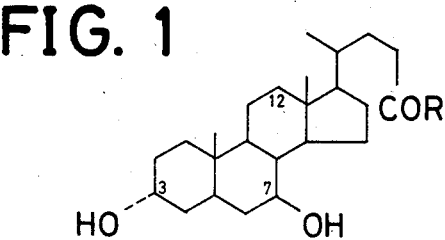
FIG. 1 is the general formula representing the structure of conjugated ursodeoxycholic acids, the final products of the method in accordance with the present invention.
Figure 2:
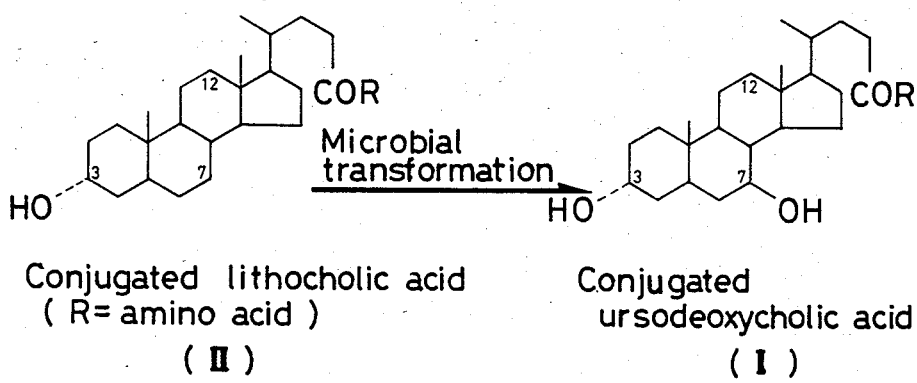
FIG. 2 is the reaction scheme representing the microbial transformation which converts conjugated lithocholic acids to conjugated ursodeoxycholic acids.
Figure 3:
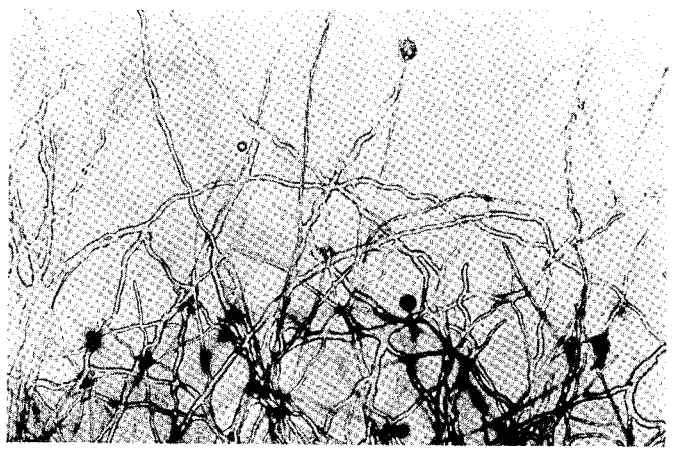
FIG. 3 is a reproduction of a micro-photograph showing the appearance of strain Y2-1, a microorganism belonging to *Mortierella ramanniana* var. *ramanniana*, which is an example of a strain which has capability of producing conjugated ursodeoxycholic acids from conjugated lithocholic acids.

FIG. 3 is a reproduction of a micro-photograph wherein the magnification is 150 showing the appearance of strain Y2-1 which was cultivated at 27° C. for one week on a malt extract agar medium containing 20 grams of malt extract, 1 gram of peptone, 20 grams of glucose, 20 grams of agar and 1 (one) liter of water and having a pH value of 6.5.

In accordance with the classification of Gams et al. (Gams W., Domsch K.H., anderson Traute - Heidi, Compendium of Soil Fungi: Academic Press, London, New York, Toronto, Sydney, San Francisco (1980), strain Y2-1 described above was identified as *Mortierella ramanniana* var. *ramanniana* and named *Mortierella ramanniana* var. *ramanniana* Y2-1. This is because the appearance of strain Y2-1 is identical to the reference appearance of *Mortierella ramanniana* and the strain requires thiamine. Strain Y2-1 has been deposited at the Fermentation Research Institute, Agency of Industrial Science & Technology, Japan with the Deposition No. FERM BP-440.

The physiological properties of strain Y2-1 are as follows:

(1) Optimum growth conditions (pH and temperature) The optimum pH range is 6 through 7, and the optimum temperature range is 27° through 28° C.

(2) Allowable growth conditions (pH and temperature) The allowable pH range is 3 through 8, and the allowable temperature range is 5° through 38° C.

(3) Other specific feature
Thiamine requirement is recognized.

(B) SCREENING OF STRAIN Y2-1

Numerous mould strains were isolated from the soil samples picked up in and adjacent to Tama district of Tokyo, Japan. Each of these mould strains was inoculated in 100 ml of a screening medium kept in a 500-ml Sakaguchi-flask, and was incubated on a shaker at 27° C. for 7 days. After completion of the incubation, the pH value of the culture (20 ml) was adjusted to 3 with 5N hydrochloric acid, before conjugated bile acids were extracted with 50 ml of n-butanol. After being dehydrated with Glauber's salt, the extract was vacuumcondensed by means of a rotary evaporator. Qualitative analysis was applied to each of the condensed extracts by means of thin layer chromatography, in order to screen any strain which is capable of producing conjugated ursodeoxycholic acids from conjugated lithocholic acids. In the aforementioned thin layer chromatography, the bands for the condensed extract were compared with those for the corresponding conjugated ursodeoxycholic acids.

In this manner, we were successful in screening a strain which was capable of producing conjugated ursodeoxycholic acids from conjugated lithocholic acids. The screened strain was named strain Y2-1. The mould strain from which we were successful in screening strain Y2-1 was isolated from the soil picked up at a field located in Yaho Kunitachi, Tokyo on July 14, 1982.

The basal medium employed for isolation of strain Y2-1 contained 1 liter of water, 50 g of glucose, 1 g of $KH_2PO_4$, 2 g of $K_2HPO_4$, 0.5 g of $MgSO_4.7H_2O$, 5 g of polypeptone, 2 g of yeast extract, 10 mg of $CaCl_2$, 10 mg of $FeSO_4.7H_2O$ and 0.5 g of conjugated lithocholic acid which was the transformational reaction substrate.

(C) EXAMPLE 1

A liquid medium is prepared by mixing 1 liter of water with 50 g of glucose, 5 g of polypeptone, 2 g of yeast extract, 2 g of $K_2HPO_4$, 1 g of $KH_2PO_4$, 0.5 g of $MgSO_4.7H_2O$, 10 mg of $CaCl_2$, 10 mg of $FeSO_4.7H_2O$, 10 mg of thiamine and 0.5 g of taurolithocholic acid. This liquid medium is employed to cultivate strain Y2-1 on a shaker at 27° C. for 48 hours in a Sakaguchi-flask. 6 liters of the aforementioned liquid medium is poured into a jar fermentor having a capacity of 10 liters. Strain Y2-1 is inoculated in the liquid medium contained in the jar fermentor by 5%, before it is cultivated under aerobic conditions at 27° C. for 5 days. During the cultivation, the agitation speed is kept at 150 rpm, the pH value is adjusted to 6, and air is supplied at the rate of 0.5 vvm. After completion of the cultivation, 5N hydrochloric acid and NaOH are added to the culture to adjust the pH value to 7. Thereafter, the cultivated microorganisms are collected out of the culture. The collected microorganisms are washed with water. A mixture of the washing liquid and a filtered liquid out of which the microorganisms are collected, is flown through a column filled with 500 g of a porous resin (Amberlite XAD-2), to allow the column to absorb the mixture of the produced conjugated ursodeoxycholic acid and the conjugated lithocholic acid remained untransformed during the above transformation process.

After the column which has absorbed the mixture is washed with water, methanol is employed to elute out the conjugated ursodeoxycholic acid and the conjugated lithocholic acid. This methanol fraction containing tauroursodeoxycholic acid is condensed by means of a rotary evaporator. This condensed methanol fraction is applied to a column in which 200 g of silica gel (Wakogel C-200) is filled, before there is applied to the column a mixture of solvents composed of isoamyl alcohol, acetic acid and water at the volumetric ratio of 18:5:3 to elute tauroursodeoxycholic acid. The elution is split into plural fractions. Out of these fractions, one or more fractions containing a high quantity of tauroursodeoxycholic acid is or are selectively collected. In this manner, tauroursodeoxycholic acid can be separated from taurolithocholic acid which is the transformational reaction substrate. A solvent containing ethanol and ethyl acetate is employed to crystallize tauroursodeoxycholic acid contained in the collected fraction or fractions.

The yield of crystallized tauroursodeoxycholic acid is 0.49 g from 1 liter of a reaction medium, representing 95% in terms of mol equivalent in comparison with the raw material.

(D) EXAMPLE 2

A liquid medium is prepared by mixing 1 liter of water with 50 g of glucose, 5 g of polypeptone, 2 g of yeast extract, 1 g of $KH_2PO_4$, 2 g of $K_2HPO_4$, 0.5 g of $MgSO_4.7H_2O$, 10 mg of $CaCl_2$, 10 mg of $FeSO_4.7H_2O$, 10 mg of thiamine and 0.5 g of glycolithocholic acid which is a transformational reaction substrate. This liquid medium is employed to incubate strain Y2-1 on a shaker at 27° C. for 48 hours in a Sakaguchi-flask. 6 liters of the aforementioned liquid medium is poured into a jar fermentor having a capacity of 10 liters. Strain Y2-1 is inoculated in the liquid medium contained in the jar fermentor by 5%, before it is cultivated under aerobic conditions at 27° C. for 5 days. During the cultivation, the agitation speed is kept at 150 rpm, the pH value is adjusted to 6, and air is supplied at the rate of 0.5 vvm.

After completion of the cultivation, 5N hydrochloric acid is added to the culture to adjust the pH value to 3. Thereafter, the conjugated bile acids are extracted with 18 liters of n-butanol. This extract is condensed by means of a rotary evaporator.

As is in the case of EXAMPLE 1, silica gel column chromatography is employed to purify the condensed extract and to elute one or more fractions containing glycoursodeoxycholic acid. Thereafter, the glycoursodeoxycholic acid contained in the fraction is crystallized from a solvent containing ethanol and ethyl acetate. The yield of crystallized glycoursodeoxycholic acid is 0.48 g from 1 liter of a reaction medium, representing 93% in terms of mol equivalent in comparison with the raw material.

Separately, the condensed extract is melted in a 15-% NaOH solution, and a deconjugation process known in the prior art is carried out at 120° C. for 5 hours, thereby free ursodeoxycholic acid is separated from glycine, though both stay in the deconjugated condensed extract. This free ursodeoxycholic acid is extracted with ethyl acetate. The ethyl acetate containing free ursodeoxycholic acid is dried by means of Glauber's salt, before being condensed by means of a rotary evaporator.

This condensed material is applied to a column in which 80 g of silica gel (Wakogel C-200) is filled, before there is applied to the column a mixture of solvents composed of chloroform, acetone, acetic acid at the volumetric ratio of 100:100:1 to elute free ursodeoxycholic acid. The elution is split into plural fractions. Out of these fractions, one or more fractions containing a high quantity of free ursodeoxycholic acid is or are selectively collected. After removing the solvent, the fractions containing free ursodeoxycholic acid are added with a small volume of ethyl acetate, thereby free ursodeoxycholic acid is crystallized.

The yield of crystallized free ursodeoxycholic acid is 0.42 g from 1 liter of a reaction medium, representing 93% in terms of mol equivalent in comparison with the raw material.

(E) EXAMPLE 3

A liquid medium is prepared by mixing 1 liter of water with 50 g of glucose, 5 g of polypeptone, 2 g of yeast extract, 1 g of $KH_2PO_4$, 2 g of $K_2HPO_4$, 0.5 g of $MgSO_4.7H_2O$, 10 mg of $CaCl_2$, 10 mg of $FeSO_4.7H_2O$ and 10 mg of thiamine. This liquid medium is employed to cultivate strain Y2-1 on a shaker at 27° C. for 48 hours in a Sakaguchi-flask. 6 liters of the aforementioned liquid medium is poured into a jar fermentor having a capacity of 10 liters. Strain Y2-1 is inoculated in the liquid medium contained in the jar fermentor by 5%, before it is cultivated under aerobic conditions at 27° C. for 108 hours. When 36 hours have passed after commencement of the inoculation, 3 g of lithocholic acid conjugated with sarcosine is poured in the jar fermentor. During the cultivation, the agitation speed is kept at 150 rpm, the pH is adjusted to 6, and air is supplied at the rate of 0.5 vvm.

A series of isolation processes which is identical to that which is employed for EXAMPLE 1, is applied to the culture to collect an ursodeoxycholic acid conjugated with sarcosine at the yield of 0.48 g per 1 liter of a reaction medium, representing 93% in terms of mol equivalent in comparison with the raw material.

(F) EXAMPLE 4

Strain Y2-1 is cultivated for 48 hours in a medium which is identical to that which is employed for EXAMPLE 1 excepting it does not contain taurolithocholic acid. The cultivated microorganisms are collected by means of a filter. After the collected microorganisms are washed with a phosphoric acid buffer having a pH value of 7.0, it is added to a reaction medium containing 1 g of $KH_2PO_4$, 2 g of $K_2HPO_4$, 10 g of glucose, 0.5 g of yeast extract, 0.2 g of glycolithocholic acid and 1 liter of water and which has a pH value of 7.0, thereby preparing a suspension containing 20 g of the microorganisms in 1 liter of the reaction medium. In this suspension, a transformational reaction is conducted under aerobic conditions at 27° C. for 48 hours.

The later processes for collection of crystallized glycoursodeoxycholic acid are identical to those which are employed for EXAMPLE 1.

The yield is 0.19 g from 1 liter of a reaction medium, representing 92% in terms of mol equivalent in comparison with the raw material.

(G) EXAMPLE 5

Strain Y2-1 is inoculated on a malt extract agar medium containing 1 liter of water with 20 g of malt extract, 1 g of polypeptone and 20 g of agar and which has the pH value of 7.0, and is cultivated at 27° C. for 1 week under aerobic conditions.

After completion of the cultivation, the cultivated microorganisms are collected and are added to a phosphoric acid buffer having the pH value of 7.0. After the buffer is filtered with a gauze filter to collect spores of the microorganism, the collected spores are washed with water, before it is added to a phosphoric acid buffer having the pH value of 7.0. The quantity of the spores in a reaction medium is adjusted to be $10^{10}$ spores/liter.

The reaction medium is added with 5 g/liter of glucose, 0.2 g/liter of yeast extract and 0.2 g/liter of taurolithocholic acid, before a transformational reaction is conducted at 27° C. for 72 hours under the conditions where sterilized air is supplied.

The later processes for collection of crystallized tauroursodeoxycholic acid are identical to those which are employed for EXAMPLE 1.

The yield is 0.19 g from 1 liter of a transformational reaction medium, representing 92% in terms of mol equivalent in comparison with the raw material.

(H) IDENTIFICATION OF PRODUCED CONJUGATED URSODEOXYCHOLIC ACIDS WITH REFERENCE URSODEOXYCHOLIC ACID

Firstly, thin layer chromatography (Merck Kieselgel G-60, $F_{254}$, 0.25-mm thick) in which development solvents for analysis of bile acids were utilized, was employed to identify each of the products of EXAMPLES 1 through 5 with the corresponding standard conjugated ursodeoxycholic acids (produced and supplied by Techno Chemical Co., Ltd.). The $R_f$ values determined for each of the products of EXAMPLES 1 through 5 are identical to the $R_f$ values determined for the corresponding standard conjugated ursodeoxycholic acid.

Additionally, various analysis tabulated below were applied to each of the products of EXAMPLES 1 through 5 to identify each of them with the aforementioned standard conjugated ursodeoxycholic acids.
1. Elemental analysis
2. Melting point test and mixed melting point test
3. Infrared spectrum analysis
4. Mass spectrum analysis
5. Nuclear magnetic resonance spectrum analysis
6. Analysis employing an equipment (manufactured by Nihon Bunko Kogyo Co., Ltd.) for high performance liquid chromatography in which a column immobilized with 3α-hydroxysteroid dehydrogenase is employed for analysis of bile acids.

The results of all the foregoing tests determined that the properties of each of the products of EXAMPLES 1 through 5 were identical to those of the corresponding standard conjugated ursodeoxycholic acid.

(I) CONCLUSION

The foregoing description has clarified that a one step method for producing conjugated ursodeoxycholic acids from conjugated lithocholic acids by means of microbial transformation has successfully been provided in accordance with the present invention and that this method has overcome the drawbacks inevitable in the aforementioned one step method for producing free ursodeoxycholic acid from free lithocholic acid by means of microbial transformation, namely a lower degree of yield, a lower reaction rate and a lower degree of productivity. In other words, this method in accordance with the present invention has various features including a higher degree of yield, a higher reaction rate and a higher degree of productivity.

Although the present invention has been described with reference to a specific strain, strain Y2-1 having its Deposition No. FERM BP-440, this is not meant to be construed in a limiting sense. Various modifications of the described embodiment, as well as other embodiments based on any of the microorganisms or moulds belonging to Mortierella, will become apparent to persons skilled in the art upon reference to the description of the present invention. It is therefore contemplated that the appended claims will cover any such modificaitons or embodiments as fall within the true scope of this invention.

What is claimed is:

1. A method for producing a ursodeoxycholic acid conjugated with an amino acid from a lithocholic acid conjugated with said amino acid by means of microbial transformation, comprising the steps of:
   cultivating a microorganism which belongs to *Mortierella ramanniana* and which has capability to produce said ursodeoxycholic acid conjugated with said amino acid from said lithocholic acid conjugated with said amino acid,
   bringing said lithocholic acid conjugated with said amino acid into contact with said microorganism to convert said lithocholic acid conjugated with said amino acid to said ursodeoxycholic acid conjugated with said amino acid, and
   recovering said ursodeoxycholic acid conjugated with said amino acid thus produced.

2. A method in accordance with claim 1, wherein said step of bringing said lithocholic acid conjugated with said amino acid into contact with said microorganism occurs in a medium in which said step of cultivating said microorganism occurs.

3. A method in accordance with claim 1, further comprising a step of harvesting said microorganism and a step of preparing a reaction medium which is a suspension containing said microorganism, and wherein said step of bringing said lithocholic acid conjugated with said amino acid into contact with said microorganism occurs in said reaction medium.

4. A method in accordance with claim 1, wherein said step of cultivating a microorganism continues until spores grow, further comprising a step of harvesting said spores and a step of preparing a reaction medium which is a suspension containing said spores, and wherein said step of bringing said lithocholic acid conjugated with said amino acid into contact with said microorganism occurs in said reaction medium.

5. A method in accordance with claim 1, wherein said microorganism is *Mortierella ramanniana* var. *ramanniana* strain Y2-1 FERM BP-440.

* * * * *